(12) United States Patent
Keropian

(10) Patent No.: US 8,132,567 B2
(45) Date of Patent: ***Mar. 13, 2012

(54) SLEEP APPLIANCE

(76) Inventor: Bryan Keropian, Tarzana, CA (US)

( * ) Notice: Subject to any disclaimer, the term of this patent is extended or adjusted under 35 U.S.C. 154(b) by 553 days.

This patent is subject to a terminal disclaimer.

(21) Appl. No.: 12/300,379

(22) PCT Filed: May 9, 2007

(86) PCT No.: PCT/US2007/011183
§ 371 (c)(1),
(2), (4) Date: Nov. 11, 2008

(87) PCT Pub. No.: WO2007/136551
PCT Pub. Date: Nov. 29, 2007

(65) Prior Publication Data
US 2009/0120448 A1   May 14, 2009

Related U.S. Application Data

(60) Provisional application No. 60/800,967, filed on May 17, 2006, provisional application No. 60/836,296, filed on Aug. 8, 2006.

(51) Int. Cl.
*A61F 5/56* (2006.01)
*A61C 3/00* (2006.01)

(52) U.S. Cl. ........................................... 128/848; 433/6

(58) Field of Classification Search ................... 128/846, 128/857, 859, 861, 848, 862; 433/6, 2, 18, 433/19, 7; 602/902
See application file for complete search history.

(56) References Cited

U.S. PATENT DOCUMENTS

| 3,871,370 | A | 3/1975 | McDonald |
| 4,669,459 | A | 6/1987 | Spiewak |
| 4,901,737 | A * | 2/1990 | Toone ........................... 128/848 |
| 5,915,385 | A | 6/1999 | Hakimi |
| 6,467,484 | B1 | 10/2002 | De Voss |
| 6,766,802 | B1 | 7/2004 | Keropian |
| 7,451,767 | B2 * | 11/2008 | Keropian ...................... 128/848 |
| 7,861,722 | B2 * | 1/2011 | Keropian ...................... 128/848 |
| 7,861,724 | B2 * | 1/2011 | Keropian ...................... 128/848 |
| 2005/0166928 | A1 | 8/2005 | Jiang |
| 2010/0224197 | A1 * | 9/2010 | Keropian ...................... 128/848 |

* cited by examiner

*Primary Examiner* — Patricia Bianco
*Assistant Examiner* — Tarla Patel
(74) *Attorney, Agent, or Firm* — Sanford Astor; Lewis Brisbois Bisgaard & Smith LLP

(57) ABSTRACT

A dental oral appliance for use with patients who suffer with sleep disorders, to reduce or eliminate snoring or obstructive sleep apnea and to open the airway for a sleeping patient. Retention for the appliance is provided by an occlusal coverage of the upper or lower teeth. A raised incisor ramp that extends from the incisal tip of the incisors toward the lingual, or posterior ramps, separate the posterior teeth to open the airway. A transpalatal member, which extends from the lingual of the right molars to the lingual of the left molars, inhibits the upward and backward movement of the tongue. The transpalatal member may be curved and may slidably fit in the body of the appliance. A posterior tongue restrainer may be attached to the transpalatal member.

29 Claims, 14 Drawing Sheets

SLEEP APPLIANCE

CROSS REFERENCE TO RELATED APPLICATIONS

The invention described in this application is an improvement over the devices described in my U.S. Pat. No. 6,766,802, issued on Jul. 27, 2004; my U.S. Pat. No. 7,451,767, issued on Nov. 18, 2008 and my U.S. Pat. No. 7,861,724, issued on Jan. 4, 2011.

STATEMENT REGARDING FEDERALLY SPONSORED RESEARCH OR DEVELOPMENT

"Not Applicable"

THE NAMES OF THE PARTIES TO A JOINT RESEARCH AGREEMENT

"Not Applicable"

INCORPORATION-BY-REFERENCE OF MATERIAL SUBMITTED ON A COMPACT DISC

"Not applicable"

BACKGROUND OF THE INVENTION (1) Field of the Invention

This invention relates to an intra-oral device for reducing or eliminating snoring and/or sleep apnea.

(2) Description of Related Art Including Information Disclosed Under 37 CFR 1.97 and 1.98

As stated in my patent referenced above, it has been estimated that ninety million American adults and children snore and that one in every ten adults snores. Snoring can have serious medical consequences for some people. Snoring is the first indication of a potentially life-threatening sleep disorder called Obstructive Sleep Apnea. If not diagnosed or if left untreated, Obstructive Sleep Apnea could result in severe medical consequences such as systemic high blood pressure, cardiovascular disease and even sudden death.

Snoring is caused by vibration of the tissues due to air turbulence as the airway narrows and may be a sign that a patient is suffering from apnea. But not all snorers suffer from apnea. Snoring can be categorized by its severity. There is the snorer who snores but experiences no physical problems. Then, there is the snorer who suffers from apnea, or the snorer who suffers from upper airway resistance. In some of these people, though they may not actually experience apneic episodes, their snoring is so loud and their breathing so labored, that it still wakes them, and their partners, numerous times throughout the night.

Many spouses, partners and/or children suffer through the night from the annoying noise of the snorer. Snoring not only disturbs the sleeping pattern of the snorer himself, it is also disruptive to the family life by causing lack of sleep to all involved. This leaves all involved unrefreshed, tired and sleepy throughout the day. It can cause sleepiness while driving, reading, working, or doing other tasks.

A broad variety of intra-oral and dental appliances and devices are now available to treat a patient for snoring. Some known oral devices for treating snoring and obstructive sleep apnea are worn inside of the mouth and work by repositioning of the jaw, moving the mandible, lifting the soft palate or moving the tongue forward. The various classes of treatment devices that now exist include mandibular advancers and tongue advancers. These appliances work by advancing the tongue and soft palate away from the back wall of the throat. Other methods used to treat snoring include controlled positive air-flow pressure systems, also known as CPAP, which require a nose mask and which are quite uncomfortable.

Other treatments for snoring include various surgeries, which are drastic steps to take to attempt to cure the problem, however snoring can be so disruptive to a person's life and relationships, that some sufferers resort to surgery.

BRIEF SUMMARY OF THE INVENTION

The sleep appliance of this invention is a dental oral appliance for use with patients who suffer with sleep disorders. Primarily it is designed to reduce or eliminate snoring and to open the airway for a sleeping individual who suffers with obstructive sleep apnea. One embodiment of the appliance is physically designed similar to an upper (maxillary) orthodontic retainer, commonly called a Hawley retainer. It covers the inside (lingual) of the upper teeth and has an open palate (nothing covering the middle area of the palate). The body of the appliance has a series of recesses to fit against the lingual side of the teeth.

Retention (holding ability) for the appliance is provided by acrylic fittings which hold the appliance in place in the same manner as an occlusal night guard.

In one embodiment, in the anterior area is a raised strip or ramp that extends from the incisal tip (biting edge) of two or more of the incisors toward the lingual. It extends back a short distance from the incisors (where they meet or touch each other). This raised anterior strip acts as a bite discluder to disclude or separate the posterior teeth.

In another embodiment there is no anterior ramp. The upper and lower teeth are separated by raised posterior ramps. This embodiment allows more room for the tongue to come forward, if desired.

There is a transverse strip, a transpalatal bar or member, that extends from the inside (lingual) of the upper or lower right molars to the inside of the upper or lower left molars. This transpalatal member extends from the right to the left and covers the tongue. It does not touch the tongue unless the tongue attempts to move upward or backward, as often happens during sleep and causes snoring or sleep apnea. The transpalatal bar inhibits and restrains the upward and backward movement of the tongue, keeping the airway open during sleep.

Optionally, the transpalatal member is curved upward at its center, so that it does not touch the tongue but passes just over the tongue when the tongue is in its normal position. Also, the transpalatal bar does not touch the palate; there is a gap between the transpalatal member and the palate. By not touching either the tongue or the palate, the device of this invention is comfortable to wear and easily tolerated by patient users. Prior art devices which have either pushed the tongue down or pressed the palate up, were found to be unusable, as they often either created a gag reflex by the user or were so uncomfortable that they were unable to be tolerated by the user. The exact radius of the curvature of the transpalatal bar is determined by the physical dimensions and structure of each individual patient's anatomy. Some patients may need little or no curvature to achieve optimum results and other patients may need more curvature. The object is to have the transpalatal bar not touch the tongue or the palate, so that it will be tolerated, but inhibit and restrain any upward or backward movement of the tongue during sleep.

In addition, in the devices of this invention, there is optionally a posterior tongue restrainer (a tail that may be straight or curved downward) that extends backward from the transpalatal bar. This posterior tongue restrainer provides a further barrier to the tongue's superior and posterior movement that blocks the airway to the posterior portion of the mouth. The posterior tongue restrainer, like the transpalatal bar, does not touch the tongue in its normal position but does restrain and inhibit the upward and backward movement of the tongue during sleep. Also, the posterior tongue restrainer, like the transpalatal bar, does not touch the palate. This posterior tongue restrainer may be added to all of the appliances that are described in my issued patent and in my co-pending application. The need for a posterior tongue restrainer depends on the needs of the patient. There may be one posterior tongue restrainer or a plurality of posterior tongue restrainers extending back from the transpalatal bar.

There is an additional embodiment, which is an appliance that covers the lower teeth, as opposed to the upper teeth, and has a transpalatal canopy bar which arcs over the tongue from right to left. The transpalatal canopy bar arches upward toward the palate and provides a cover (restrainer) over the tongue, but it does not touch the palate. A posterior tongue restrainer may be added to this arched transpalatal bar. This arched transpalatal canopy bar does not touch the tongue or the palate but inhibits and restrains the upward and backward movement of the tongue during sleep.

In addition, the transpalatal bar, with or without the posterior tongue restrainer, in all versions of the appliance, may be made adjustable, anterior to posterior, by providing a slidable fit of the transpalatal bar, forward and backward. With this adjustment, the appliance can be customized to each patient, to provide the proper fit for inhibiting movement of the tongue of each patient at its maximum effectiveness.

The slidable transpalatal bar fits into slots or grooves on either side of the lingual (palate side) of the appliance and can slide forward and backward. The position of the transpalatal bar is determined by the patient's comfort. If it bothers the patient and causes gagging, then it is slid forward. If there is no problem with comfort, it is moved all the way back. If it requires being slid forward, it is worn for a month or so in this position, then slid all the way back. In almost all cases, the patient can then tolerate the bar all the way back. When the optimum location of the bar is determined, it is then cemented into place with acrylic.

To understand the effectiveness of the appliance, the mechanism of snoring and obstructive sleep apnea must be understood. While we sleep, the tongue falls back and up towards the palate and it partially or completely obstructs or closes the airway path. This results in snoring, obstructive sleep apnea, or Upper Airway Resistance Syndrome. The medical treatment for these maladies ranges from medication to a CPAP (Continuous Positive Airway Pressure) machine. The CPAP is nearly 100% successful when utilized. Unfortunately, the non-compliance for CPAP use ranges from 50% to 80% depending where one searches in the literature. The American Association of Sleep Medicine designated dental sleep appliances as the number one alternative to CPAP for moderate snoring.

The sleep appliance of this invention is designed to treat the problem of tongue blockage when sleeping. It works by utilizing several factors. First, it changes the vertical dimension (height of the opening or separation of the teeth). This results in an increased opening of the airway. Second, the transpalatal member that runs transverse along the back of the appliance effectively inhibits and restrains any upward or backward movement of the tongue that would block the airway opening during sleep. Optionally, if needed, the sleep appliance can also include mandibular advancement to increase the opening, thus increasing the airway.

Accordingly, it is an object of this invention to provide a simple device to prevent or reduce snoring as well as Obstructive Sleep Apnea.

It is another object of this invention to provide a device, easily applied and easily tolerated, which will substantially prevent snoring.

Further objects and advantages will become apparent from a consideration of the following description and drawings.

BRIEF DESCRIPTION OF THE SEVERAL VIEWS OF THE DRAWING(S)

DETAILED DESCRIPTION OF THE INVENTION

Figure 1:
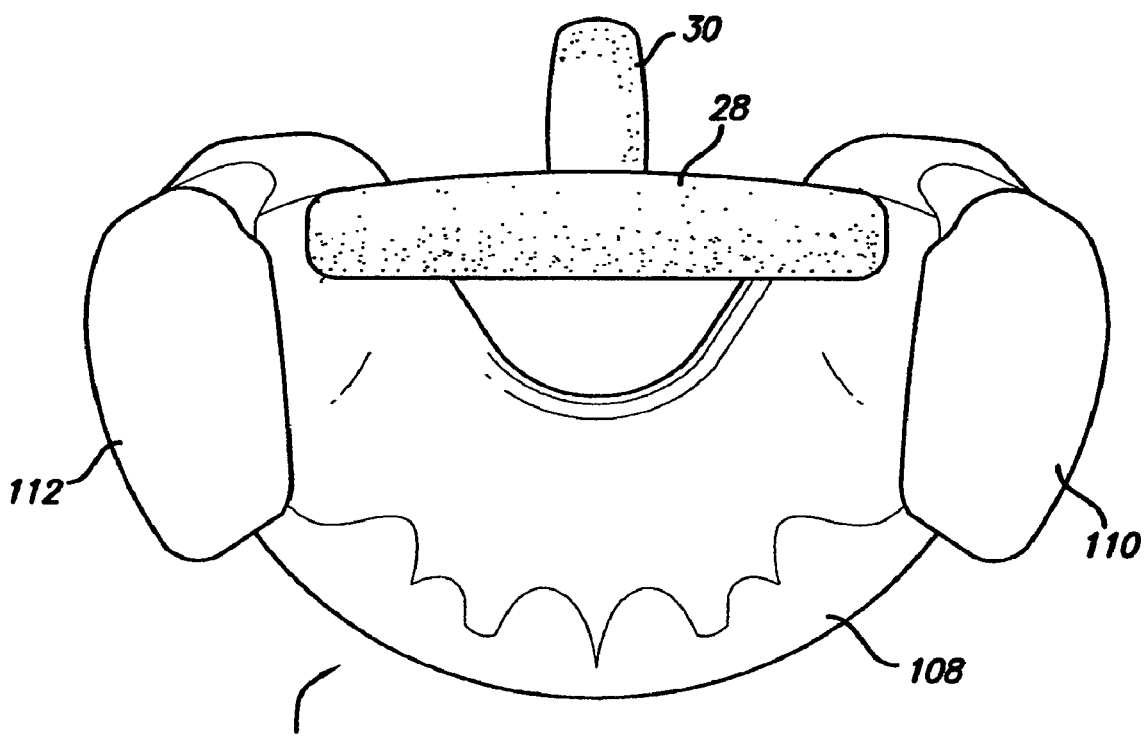
FIG. 1 is a bottom view of an embodiment of the improved sleep appliance of this invention.

Referring now to FIG. 1, there is shown a first embodiment 106 of the sleep appliance of this invention comprising a body 108. Body 108 is made entirely of an acrylic plastic, commonly used for dental devices, and is custom fitted to fit over the wearer's posterior teeth in the same manner as an occlusal night guard, which uses an occlusal coverage. The occlusal coverage holds appliance 106 firmly onto the posterior teeth.

Raised posterior ramps 10 and 112 provide a surface against which the lower teeth occlude. Transpalatal bar 28 inhibits the upward and backward movement of the tongue to keep the airway open during sleep. With no anterior strip or ramp, the tongue can come forward increasing the airway flow. Posterior tongue restrainer 30 (which may be straight or curved downward) is attached to the center rear portion of transpalatal bar 28 and extends rearward to further inhibit the upward and backward movement of the tongue Referring now to FIG. 2, there is shown a second embodiment comprising sleep appliance 40 having a body 42. Body 42 is made entirely of an acrylic plastic, commonly used for dental devices, and is custom fitted to fit over the wearer's posterior teeth in the same manner as an occlusal night guard which uses an occlusal coverage. The occlusal coverage holds appliance 40 firmly onto the posterior teeth.

There is a raised anterior strip 44 that extends from the incisal tip (biting edge) of two or more of the incisors toward the lingual. Strip 44 extends back a short distance from the middle of the central incisors. Strip 44 acts as a bite discluder, separating the posterior teeth. Strip 44 is preferably from about 3 mm to about 5 mm thick in order to separate the posterior teeth.

Transpalatal bar 28 inhibits the upward and backward movement of the tongue to keep the airway open during sleep. Posterior tongue restrainer 30 is attached to the center rear portion of transpalatal bar 28 and extends rearward to further inhibit the upward and backward movement of the tongue.

Figure 2:
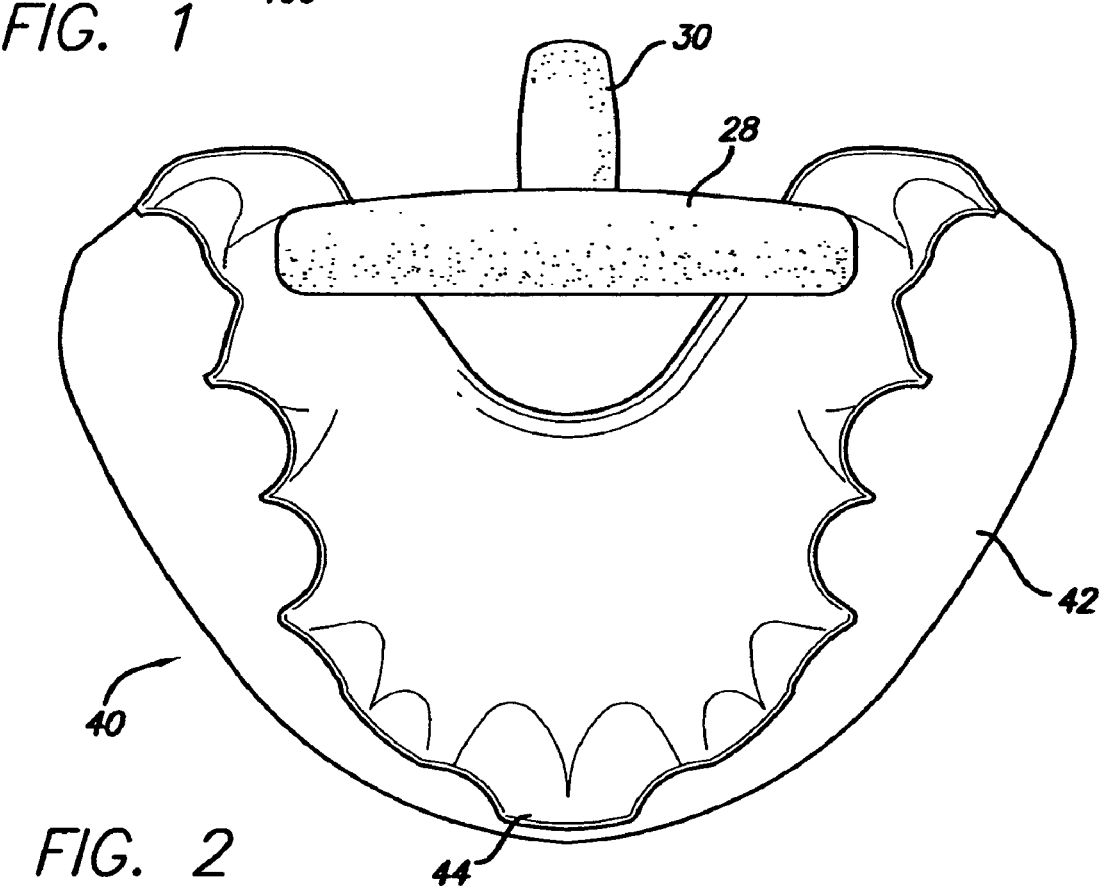
FIG. 2 is a bottom view of another embodiment.
Figure 3:
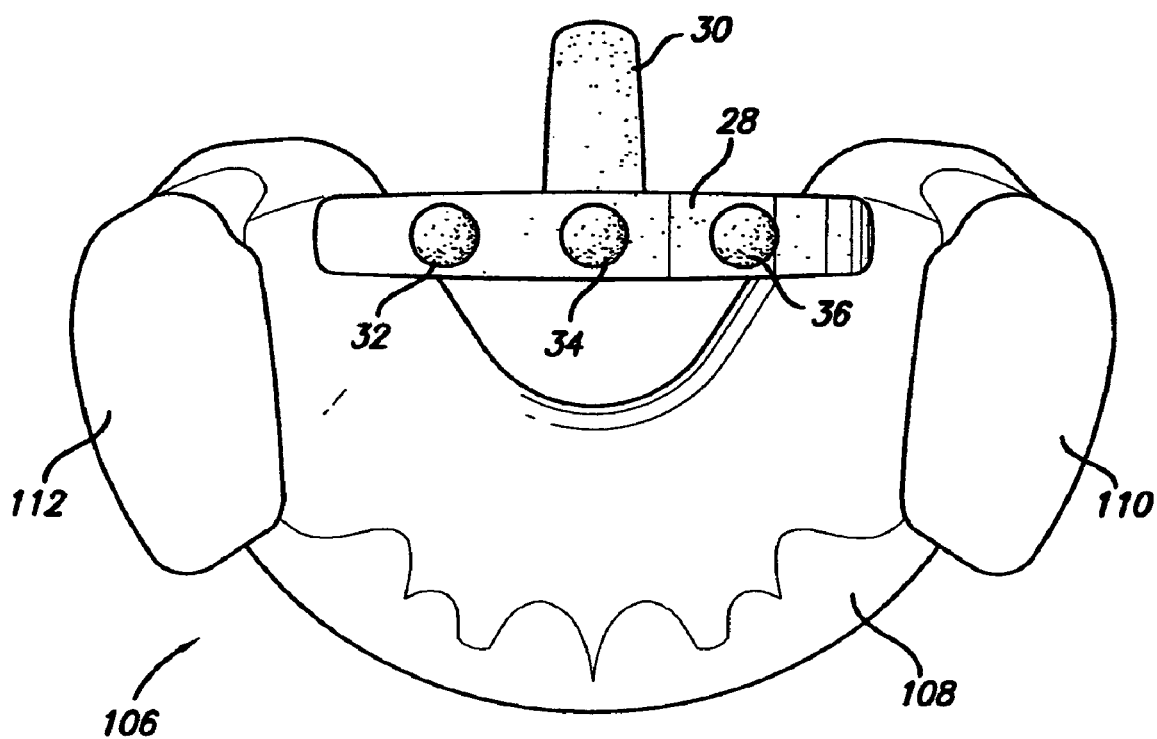
FIG. 3 is a bottom view of the embodiment of FIG. 1 with projections on the transpalatal bar.
Figure 4:
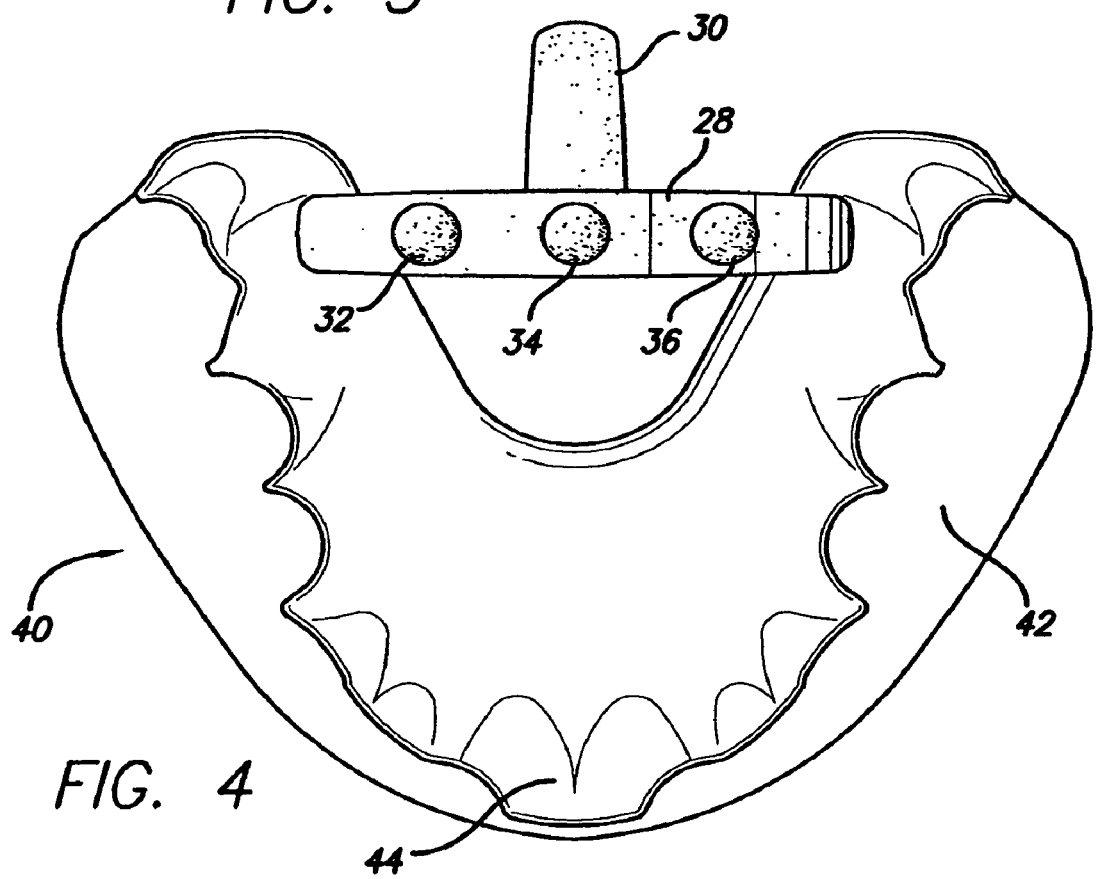
FIG. 4 is a bottom view of the embodiment of FIG. 2 with projections on the transpalatal bar.

FIGS. 3 and 4 show the same appliances shown in FIGS. 1 and 2 but have added posterior projections 32, 34 and 36 added to the bottom of transpalatal bar 28, to further inhibit the upward and backward movement of the tongue. Posterior projections 32, 34 and 36 may be from about 1 mm to about 6 mm long depending upon the needs of the patient. While three projections are shown and are cylindrical in shape, any number, from about 2 to about 12 projections may be used and they may be any shape, such as rectangular, conical, oval, or any other shape.

Figure 5A:
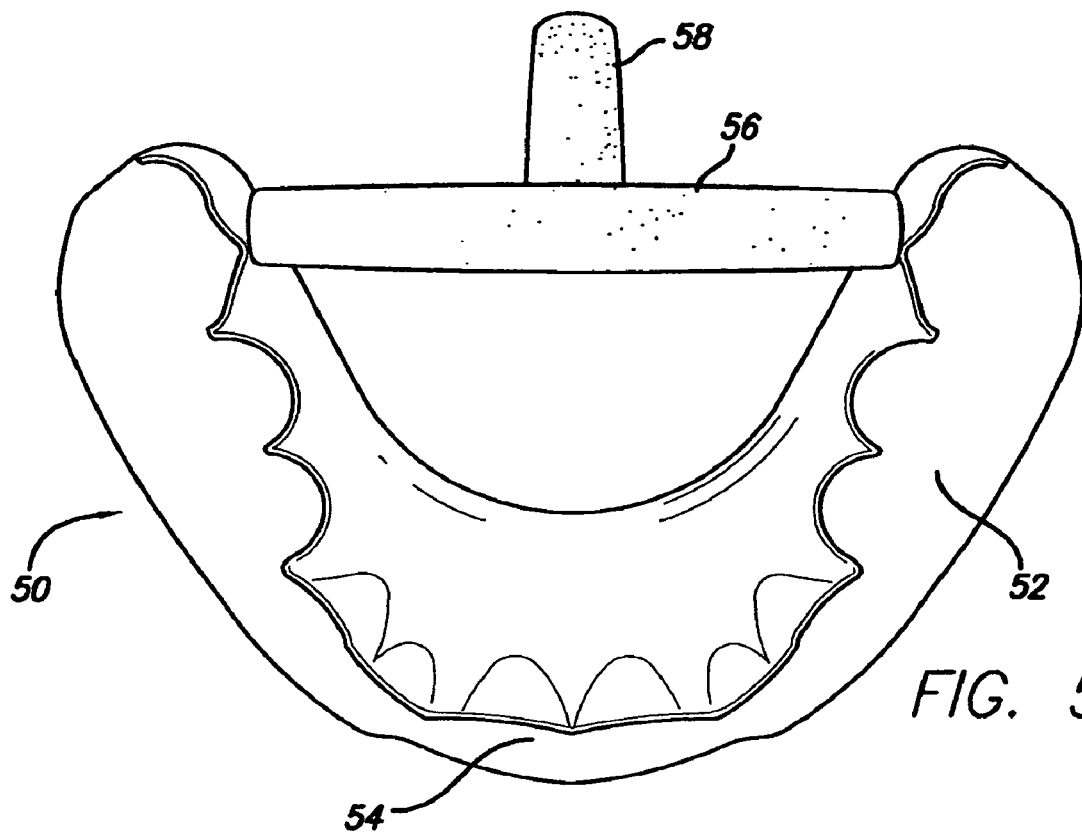
FIG. 5A is a top view of an embodiment of the device for attachment to the lower teeth and having posterior tongue restrainer.
Figure 5B:
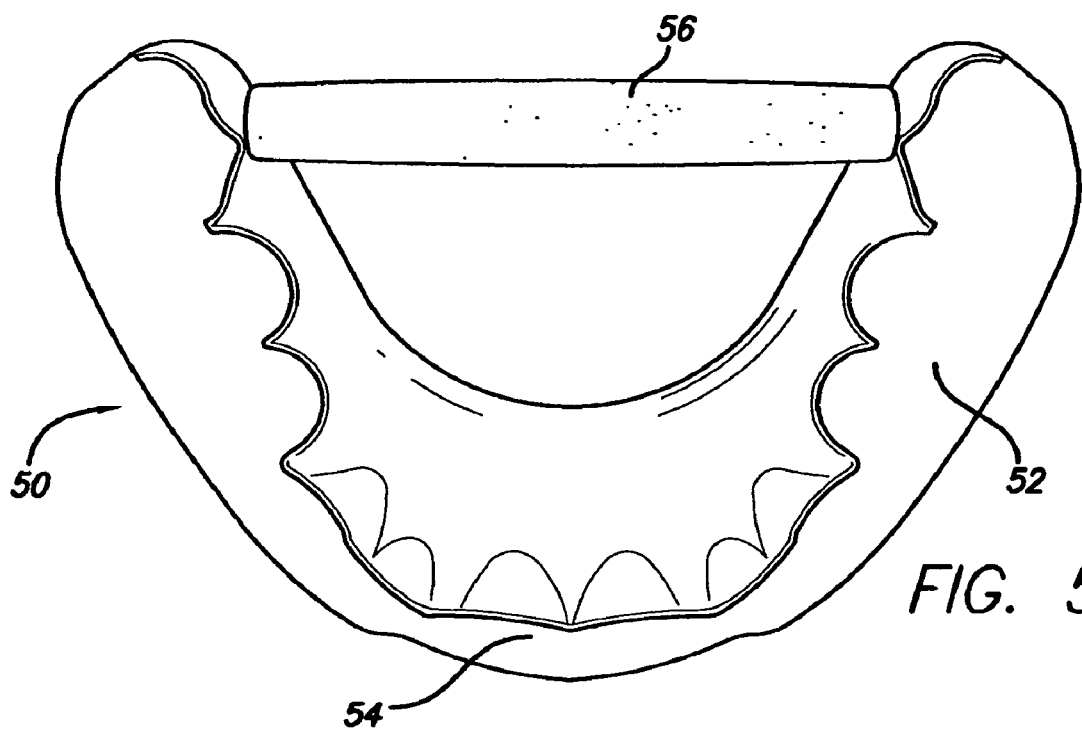
FIG. 5B is a top view of the embodiment of FIG. 5A without the posterior tongue restrainer.

Referring to FIGS. 5A and 5B there is shown another embodiment of an appliance 50 with a body 52 and an anterior strip or ramp 54. This appliance is adapted to fit over the lower teeth rather than the upper teeth. Body 52 is made entirely of an acrylic plastic, commonly used for dental devices, and is custom fitted to fit over the wearer's lower posterior teeth in the same manner as an occlusal night guard, which uses an occlusal coverage. The occlusal coverage holds appliance 50 firmly onto the lower posterior teeth.

Transpalatal bar 56 inhibits the upward and backward movement of the tongue. Posterior tongue restrainer 58, in the device shown in FIG. 5A, optionally not on the device shown in FIG. 5B, is attached to the center rear portion of transpalatal bar 56 and extends rearward to further inhibit the upward and backward movement of the tongue.

Transpalatal bar 56 is arched to fit over the tongue to inhibit the upward and backward movement of the tongue, the arch being required because the device 50 is fitted over the lower teeth, as opposed to the upper teeth as shown in the previous embodiments. Posterior projections, such as 32, 34 and 36 shown in FIGS. 3 and 4, may also be present if needed for the patient's benefit.

The presence or absence of the posterior tongue restrainer or the posterior projections, as well as the particular type of appliance from the various embodiments shown, is chosen based upon what works best for the individual patient.

Figure 5C:
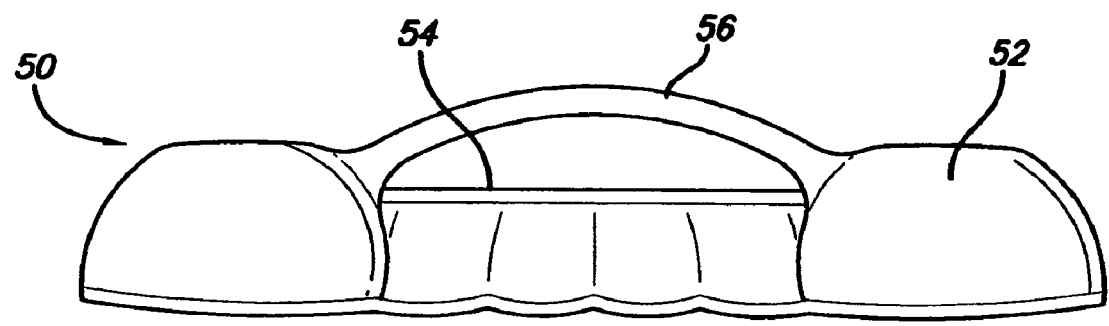
FIG. 5C is a rear view of the embodiment of FIG. 5A.

Referring now to FIG. 5C, there is shown a rear view of the appliance shown in FIG. 5B to show the arched shape of transpalatal canopy bar 56.

Figure 6:
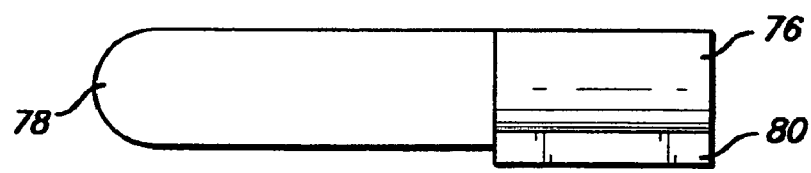
FIG. 6 is a side elevational view of the slidable posterior tongue restrainer.
Figure 7:
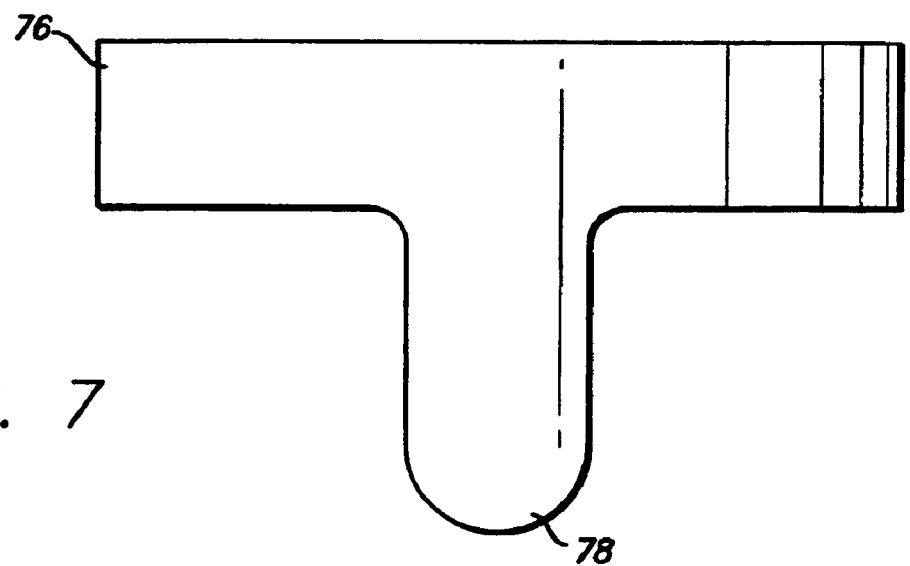
FIG. 7 is a top view of the slidable posterior tongue restrainer.
Figure 8:
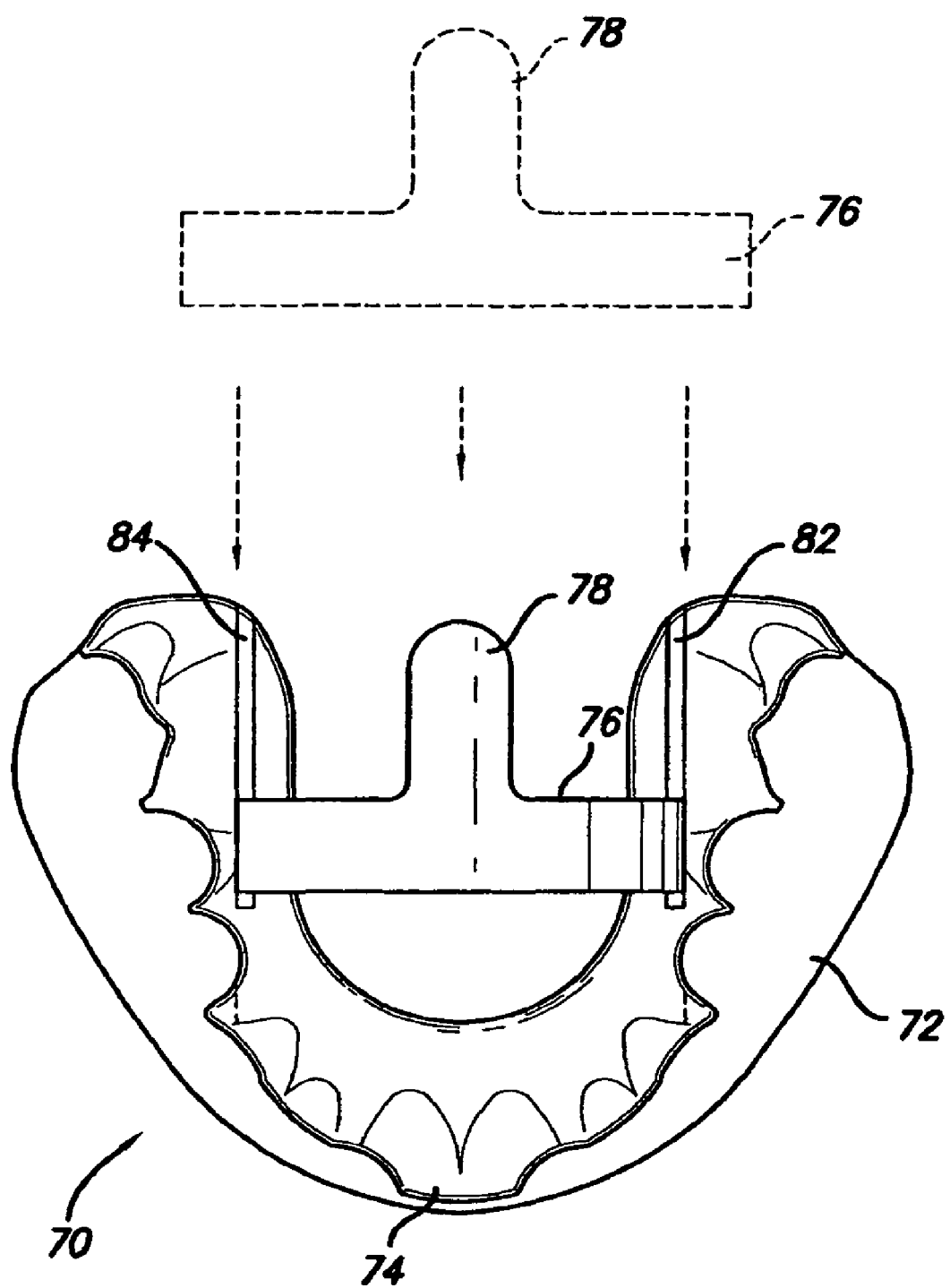
FIG. 8 is a bottom view of one embodiment of the device with a slidable posterior tongue restrainer; and, FIG. 9 is a bottom view of another embodiment with a slidable posterior tongue restrainer.

Referring now to FIGS. 6, 7 and 8 there is shown another embodiment comprising an appliance 70 having a body 72 and an anterior strip or ramp 74, the same construction as the device shown in FIG. 2. Transpalatal bar 76, having posterior tongue restrainer 78, is slidably held in body 72. There are two narrow slots 82 and 84 into which two narrow ribs 80, shown in FIG. 6, (and the other rib on the other side of transpalatal bar 76, which is hidden and not shown) are slidably engaged. This allows adjustment of transpalatal bar 76 having posterior tongue restrainer 78 in an anterior/posterior direction, to custom fit the device for the best fit for the patient. Once the desired best fit is determined, the transpalatal bar 76 is locked in place by the addition of a bit of fluid acrylic, which dries quickly and bonds transpalatal bar 76 in place.

Figure 9:
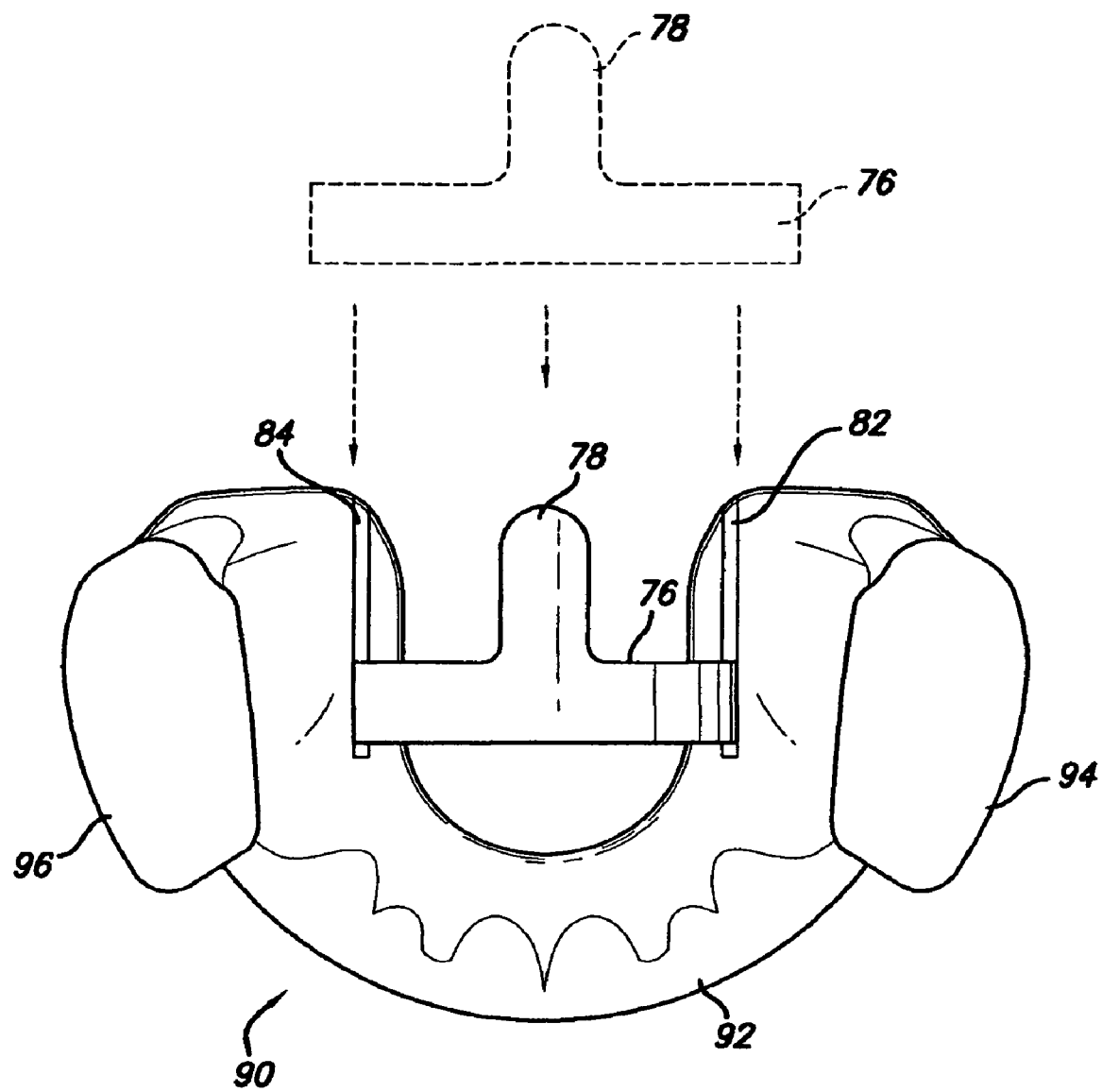

Referring now to FIG. 9, there is shown another embodiment having the same basic structure as the appliance of FIG. 1. The appliance 90 has a body 92 and raised posterior ramps 94 and 96. The slidable transpalatal bar 76 with posterior tongue restrainer 78 is the same as shown in FIG. 8.

Figure 10:
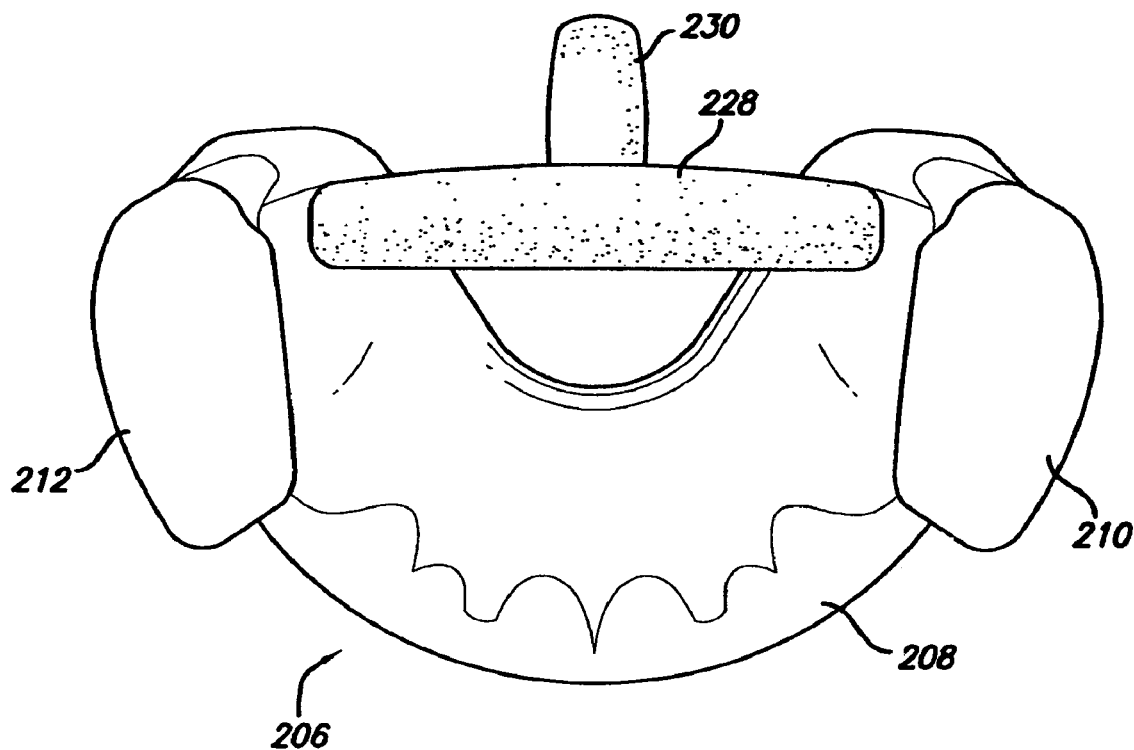
FIG. 10 is a bottom view of another embodiment of the improved sleep appliance of this invention.
Figure 11:
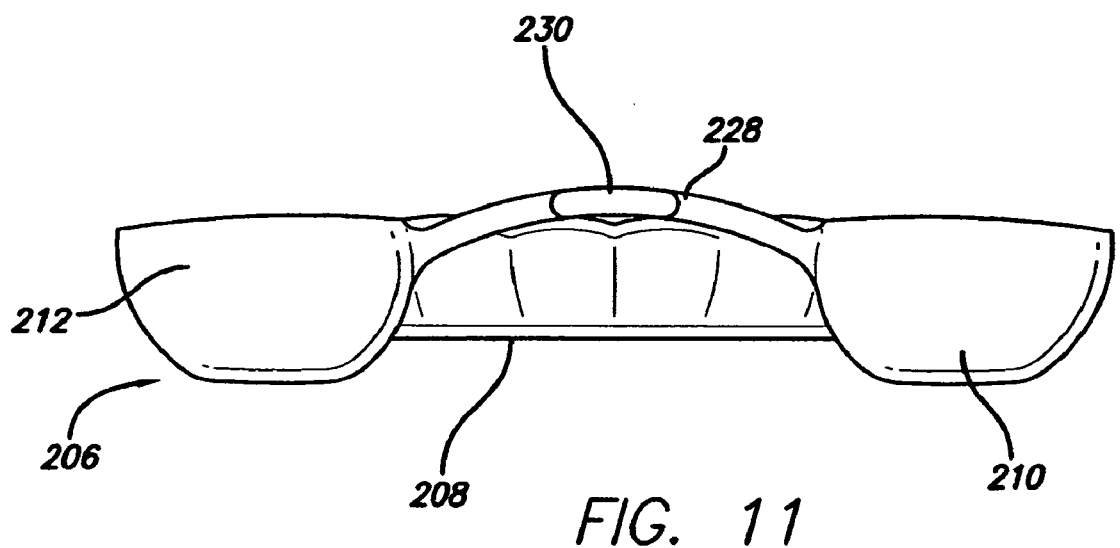
FIG. 11 is a rear view of the appliance of FIG. 10.

Referring now to FIGS. 10, and 11, there is shown an embodiment 206 of the sleep appliance of this invention comprising a body 208. Body 208 is made entirely of an acrylic plastic, commonly used for dental devices, and is custom fitted, to fit over the wearer's posterior teeth in the same manner as an occlusal night guard, which uses an occlusal coverage. The occlusal coverage holds appliance 206 firmly onto the upper posterior teeth.

Raised posterior ramps 210 and 212 provide a surface against which the lower teeth occlude. Transpalatal bar 228 has a curved shape, curving slightly upward at the middle to cover, but not touch the tongue. With no anterior ramp, the tongue can come forward increasing the airway flow. Posterior tongue restrainer 230 is attached to the center rear portion of transpalatal bar 228 and extends rearward to further inhibit and restrain the upward and backward movement of the tongue during sleep. Posterior tongue restrainer 230 does not touch the tongue or the palate but is present to aid in inhibiting and restraining the upward and backward movement of the tongue during sleep, to keep the airway open.

Figure 12:
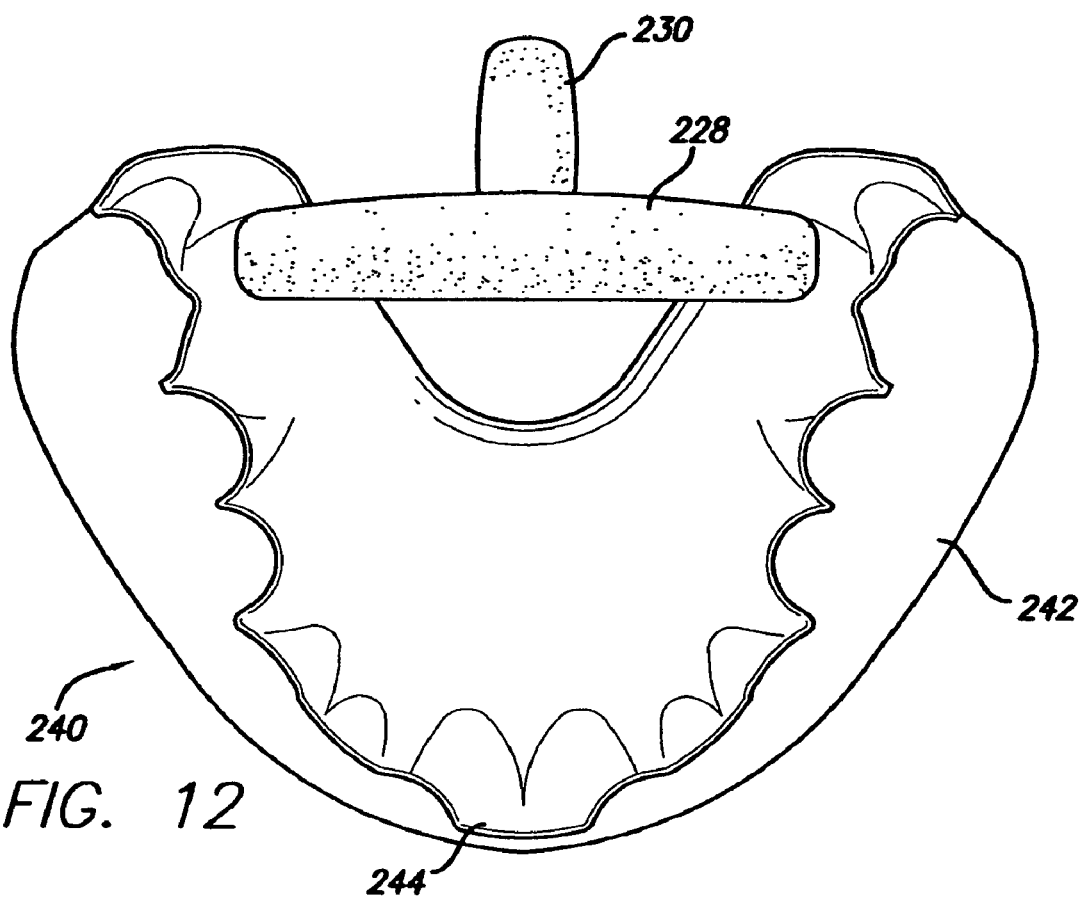
FIG. 12 is a bottom view of another embodiment.

Referring now to FIG. 12, there is shown another embodiment comprising sleep appliance 240 having a body 242. Body 242 is made entirely of an acrylic plastic, commonly used for dental devices, and is custom fitted to fit over the wearer's posterior teeth in the same manner as an occlusal night guard, which uses an occlusal coverage. The occlusal coverage holds appliance 240 firmly onto the posterior teeth.

There is a raised anterior strip 244 that extends from the incisal tip (biting edge) of two or more of the incisors toward the lingual. Strip 244 extends back a short distance from the middle of the central incisors, for about one-half inch. Strip 244 acts as a bite discluder, separating the posterior teeth. Strip 244 is preferably from about 3 mm to about 5 mm thick in order to separate the posterior teeth.

Transpalatal bar 228 is curved as described in FIG. 10 to inhibit and restrain the upward and backward movement of the tongue during sleep. Posterior tongue restrainer 230 is attached to the center rear portion of transpalatal bar 228 and extends rearward to further inhibit and restrain the upward and backward movement of the tongue during sleep. Transpalatal bar 28 is preferably about ⅛ inch to about ½ inch wide. Posterior tongue restrainer 230 is preferably about ¼ inch to about 1 inch long and about ⅛ inch to about ½ inch wide.

Figure 13:
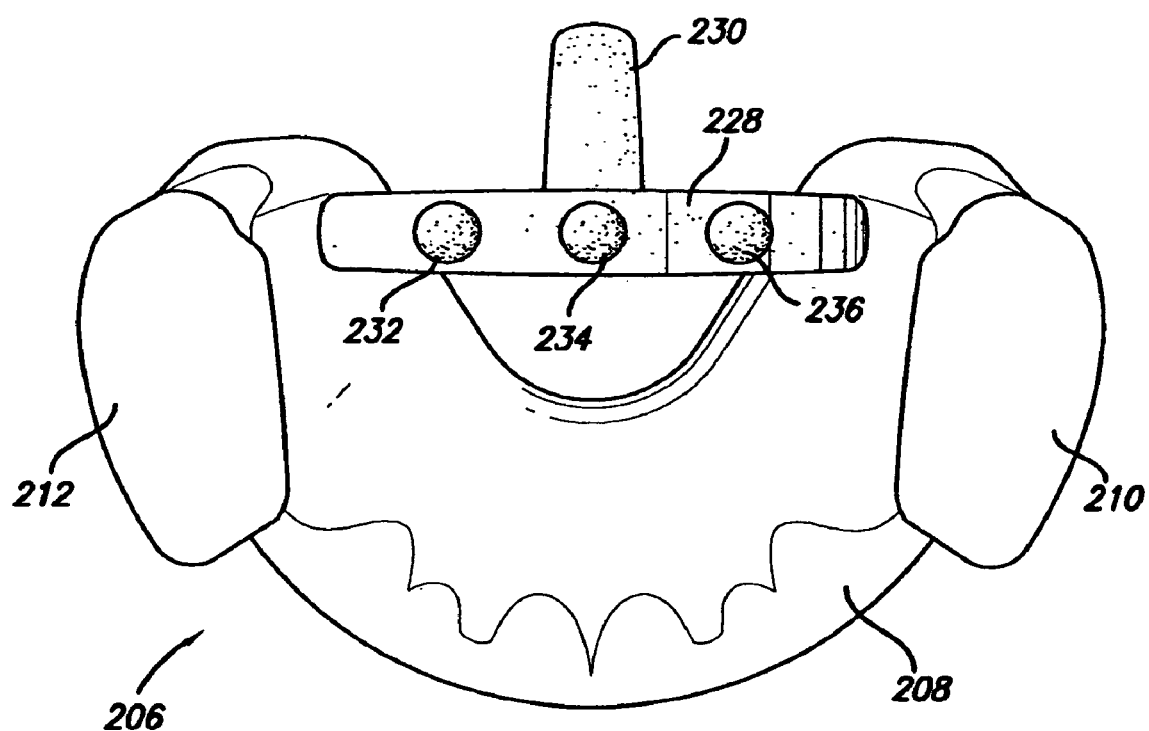
FIG. 13 is a bottom view of the embodiment of FIG. 11 with projections on the transpalatal bar.
Figure 14:
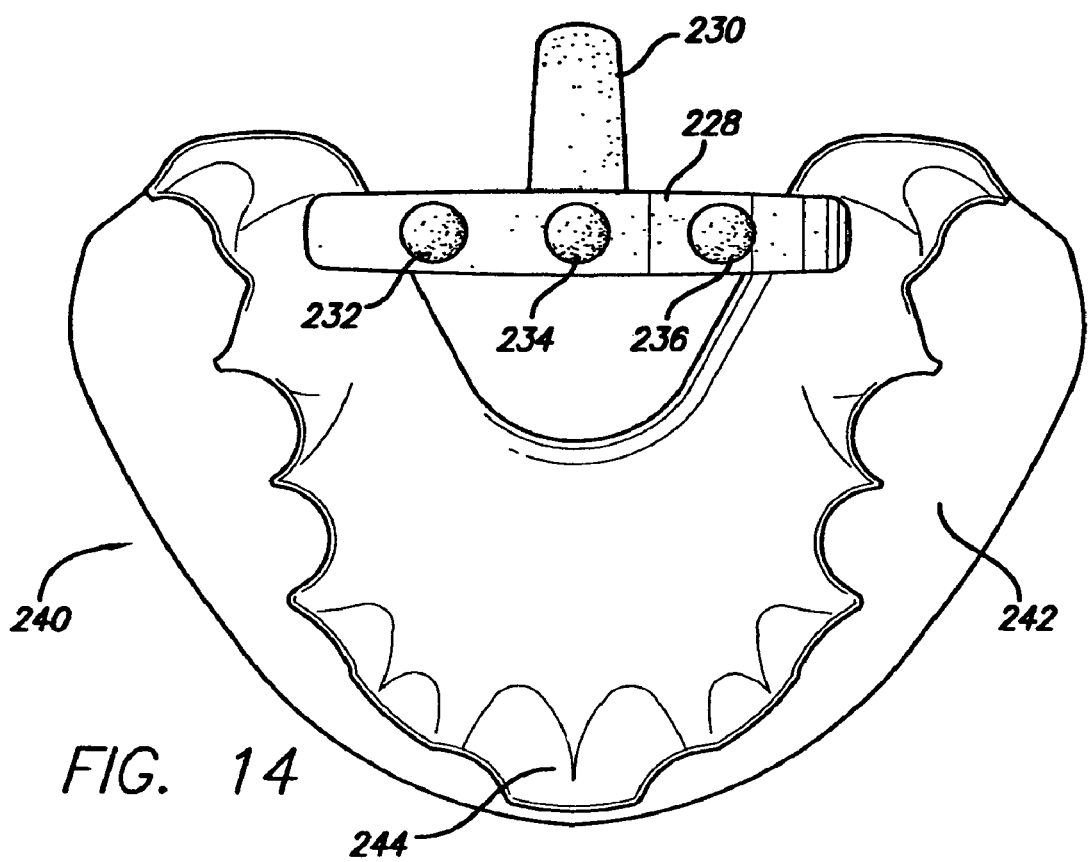
FIG. 14 is a bottom view of the embodiment of FIG. 12 with projections on the transpalatal bar.

FIGS. 13 and 14 show the same appliances shown in FIGS. 10 and 12 but have added posterior projections 232, 234 and 236 added to the bottom of transpalatal bar 228, to further inhibit and restrain the upward and backward movement of the tongue during sleep. Posterior projections 232, 234 and 236 may be from about 1 mm to about 6 mm long depending upon the needs of the patient. While three projections are shown and are cylindrical in shape, any number, from about 2 to about 12 projections may be used and they may be any shape, such as rectangular, conical, oval, or any other shape. The projections do not touch the tongue in its normal position but in certain cases are needed to further inhibit and restrain the upward and backward movement of the tongue during sleep.

Figure 15A:
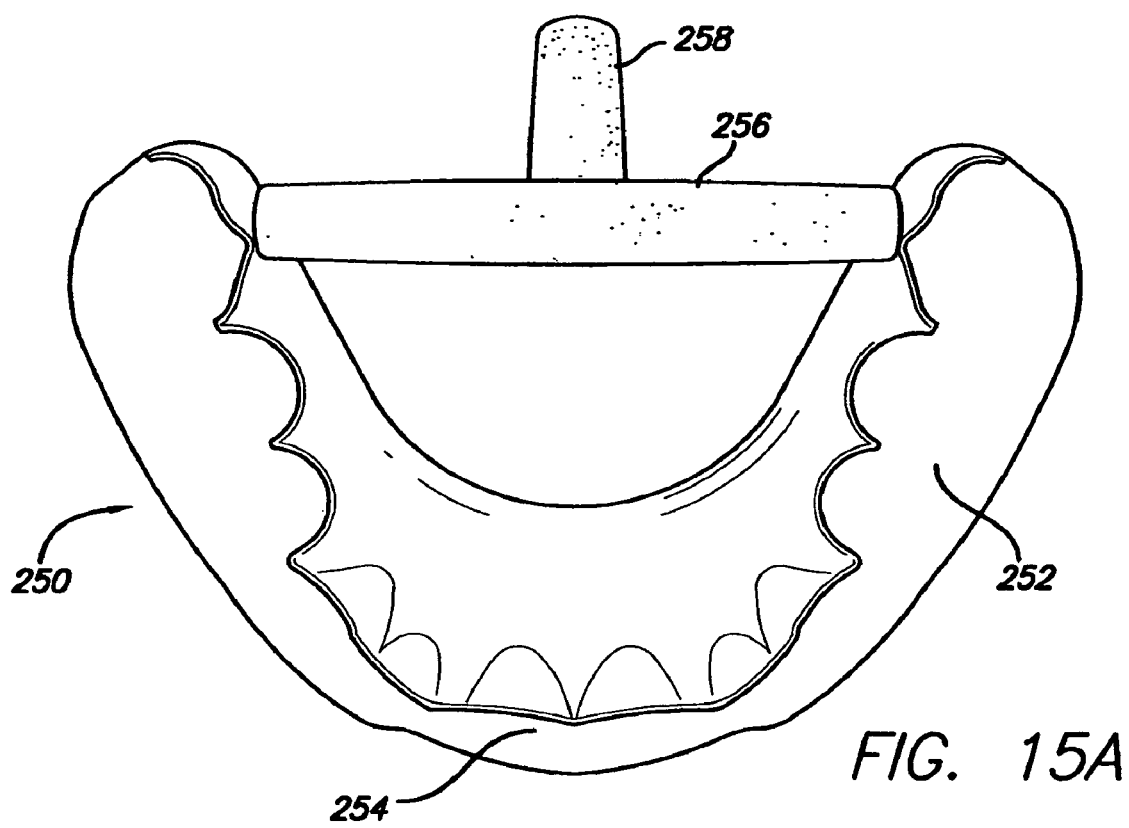
FIG. 15A is a top view of an embodiment of the device for attachment to the lower teeth.
Figure 15B:
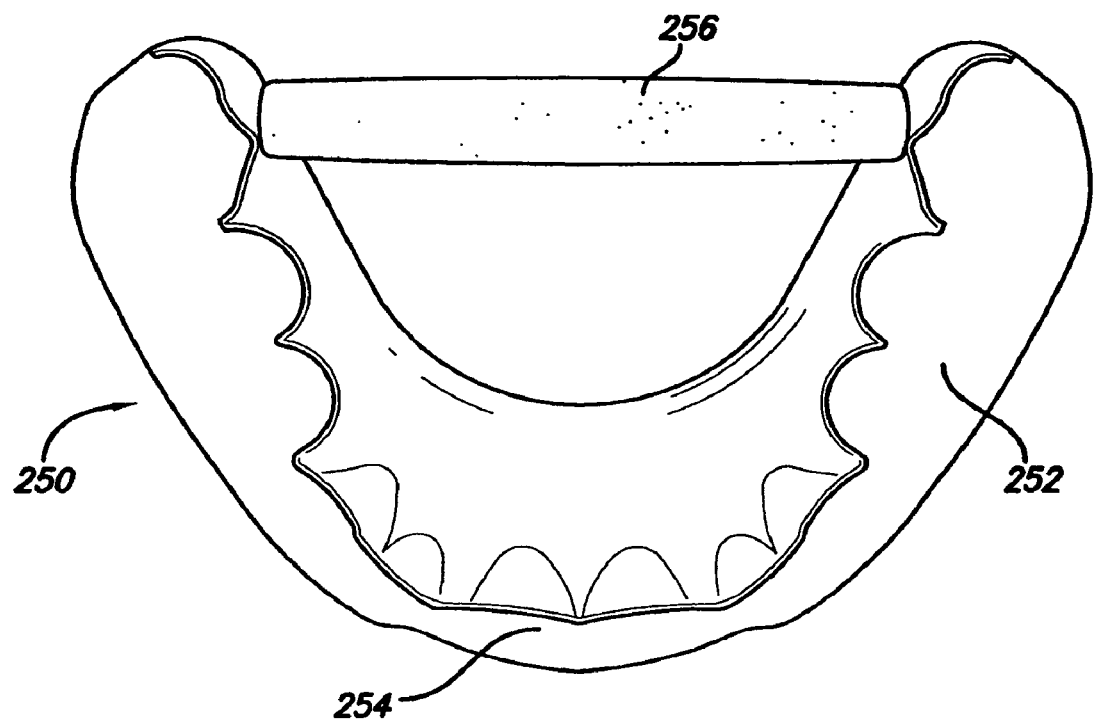
FIG. 15B is a top view of the embodiment of FIG. 15A without the posterior tongue restrainer.
Figure 15C:
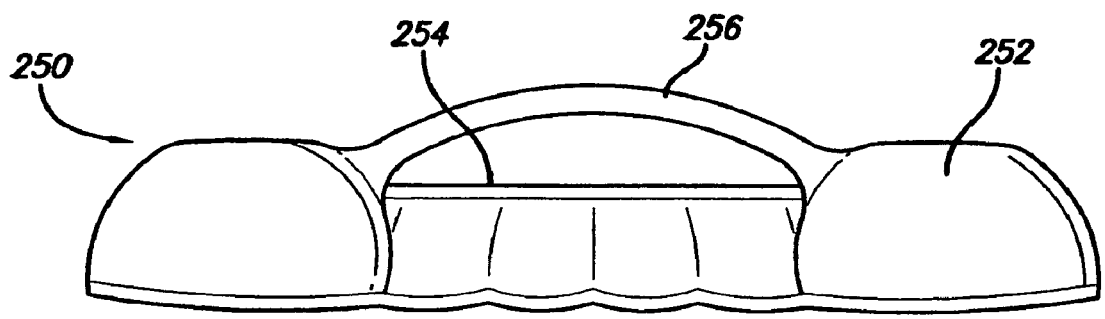
FIG. 15C is a rear view of the embodiment of FIG. 15A.

Referring to FIGS. 15A, 15B and 15C there is shown another embodiment of an appliance 250 with a body 252 and an anterior strip or ramp 254. This appliance is adapted to fit over the lower teeth rather than the upper teeth. Body 252 is made entirely of an acrylic plastic, commonly used for dental devices, and is custom fitted to fit over the wearer's lower posterior teeth in the same manner as an occlusal night guard, which uses an occlusal coverage. The occlusal coverage holds appliance 250 firmly onto the lower posterior teeth.

Transpalatal bar 256 acts in the same manner as described for the above-described embodiments. Posterior tongue restrainer 258, in the device shown in FIG. 15A, optionally not on the device shown in FIG. 15B, is attached to the center rear portion of transpalatal bar 256 and extends rearward to further inhibit and restrain the upward and backward movement of the tongue during sleep.

Transpalatal bar 256 is arched to fit over the tongue but not touch it in its normal state, see FIG. 15C. The arch is required because the device 250 is fitted on the lower teeth, as opposed to the upper teeth, as shown in previous embodiments. Posterior projections, such as 232, 234 and 236 shown in FIGS. 13 and 14, may also be present if desired.

The presence or absence of the posterior tongue restrainer or the posterior projections, as well as the particular type of appliance from the various embodiments shown, is chosen based upon what works best for the individual patient.

Figure 16:
FIG. 16 is a side elevational view of an adjustable transpalatal bar with a posterior tongue restrainer.
Figure 17:
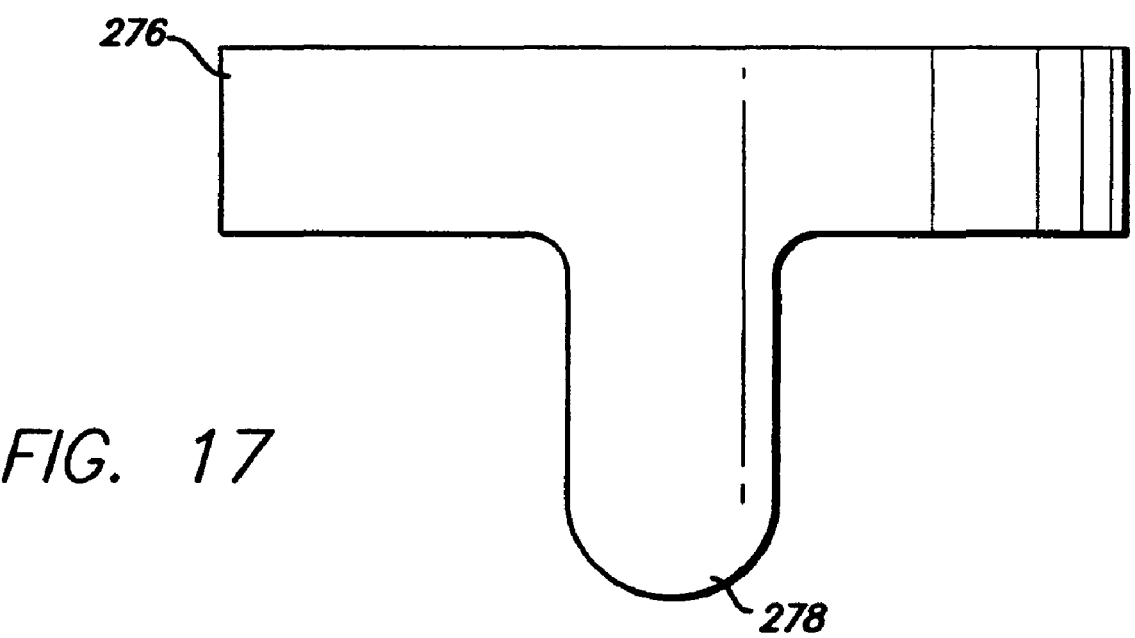
FIG. 17 is a top view of a transpalatal bar with a posterior tongue restrainer.
Figure 18:
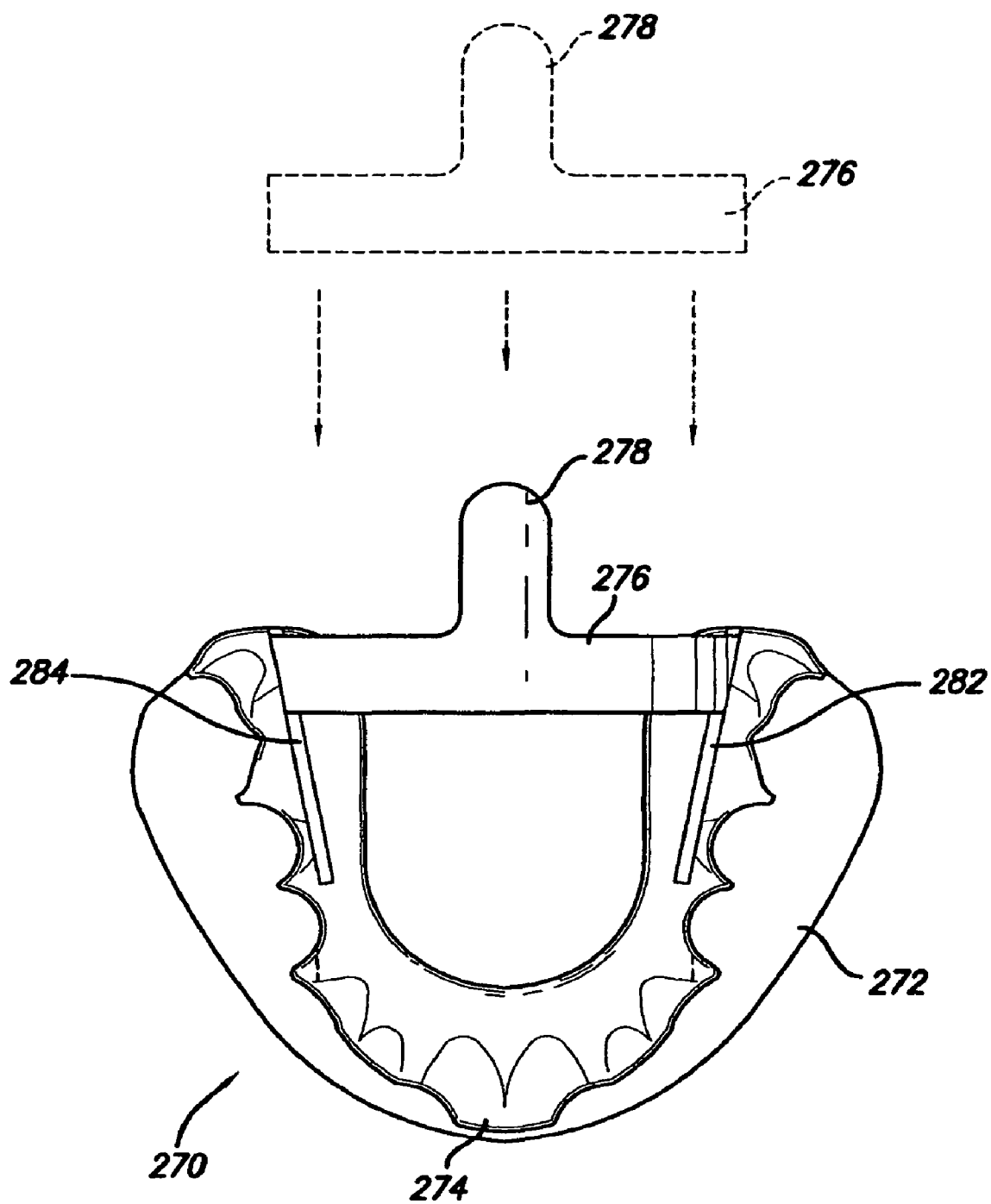
FIG. 18 is a bottom view of one embodiment of the device with an adjustable transpalatal bar having a posterior tongue restrainer.

Referring now to FIGS. 16, 17 and 18 there is shown another embodiment comprising an appliance 270 having a body 272 and an anterior ramp 274, the same construction as the device shown in FIG. 12. Transpalatal bar 276, which is curved as described in previous devices described herein, is slidably held in body 272. Posterior tongue restrainer 278 is attached to transpalatal bar 276. There are two narrow grooves or slots 282 and 284 into which the outer ends of transpalatal bar 276 fit and are slidably engaged. In this embodiment ribs 80, such as shown in FIG. 6, are not required. Grooves 282 and 284 narrow slightly towards the front end of the device. This may be necessary due to the shape of the body 272. This allows adjustment of transpalatal bar 276 having posterior tongue restrainer 278 in an anterior/posterior direction, to custom fit the device for the best fit for the patient. Transpalatal bar 276 can slide a short distance in slots 282 and 284. If more movement is needed, the dentist attending will have to remove the bar 276 and cut a portion off of the ends and replace the ends in slots 282 and 284. Once the desired best fit is determined, transpalatal bar 276 is locked in place by the addition of a bit of fluid acrylic, which dries quickly and bonds transpalatal bar 276 in place.

Figure 19:
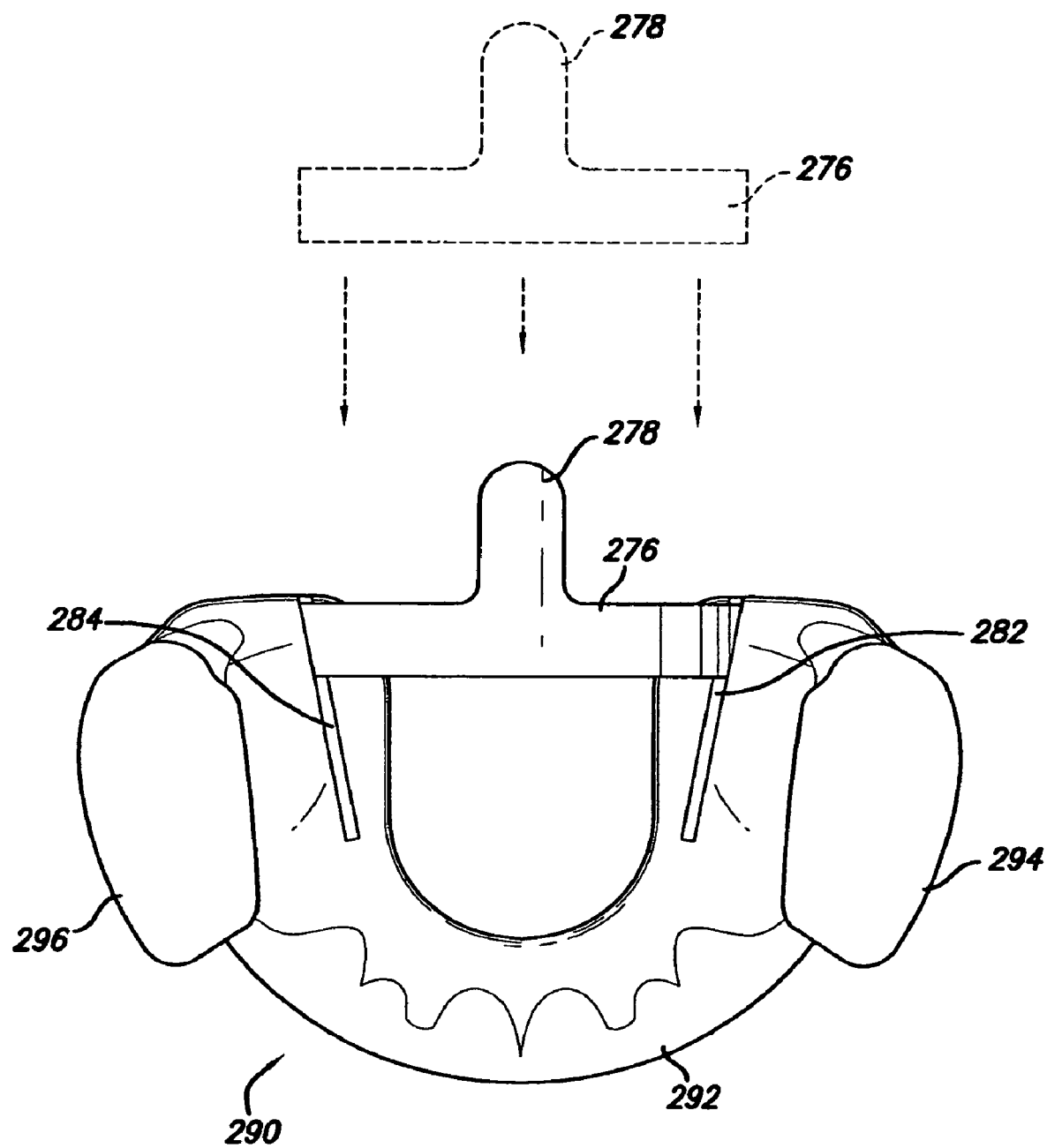
FIG. 19 is a bottom view of another embodiment with an adjustable transpalatal bar having a posterior tongue restrainer; and, FIG. 20 is a bottom view of the appliance of FIG. 19 without a posterior tongue restrainer.

Referring now to FIG. 19, there is shown another embodiment having the same basic structure as the appliance of FIG. 10. The appliance 290 has a body 292 and raised posterior ramps 294 and 296. The slidable transpalatal bar 276 with posterior tongue restrainer 278 is the same as shown in FIG. 18.

Figure 20:
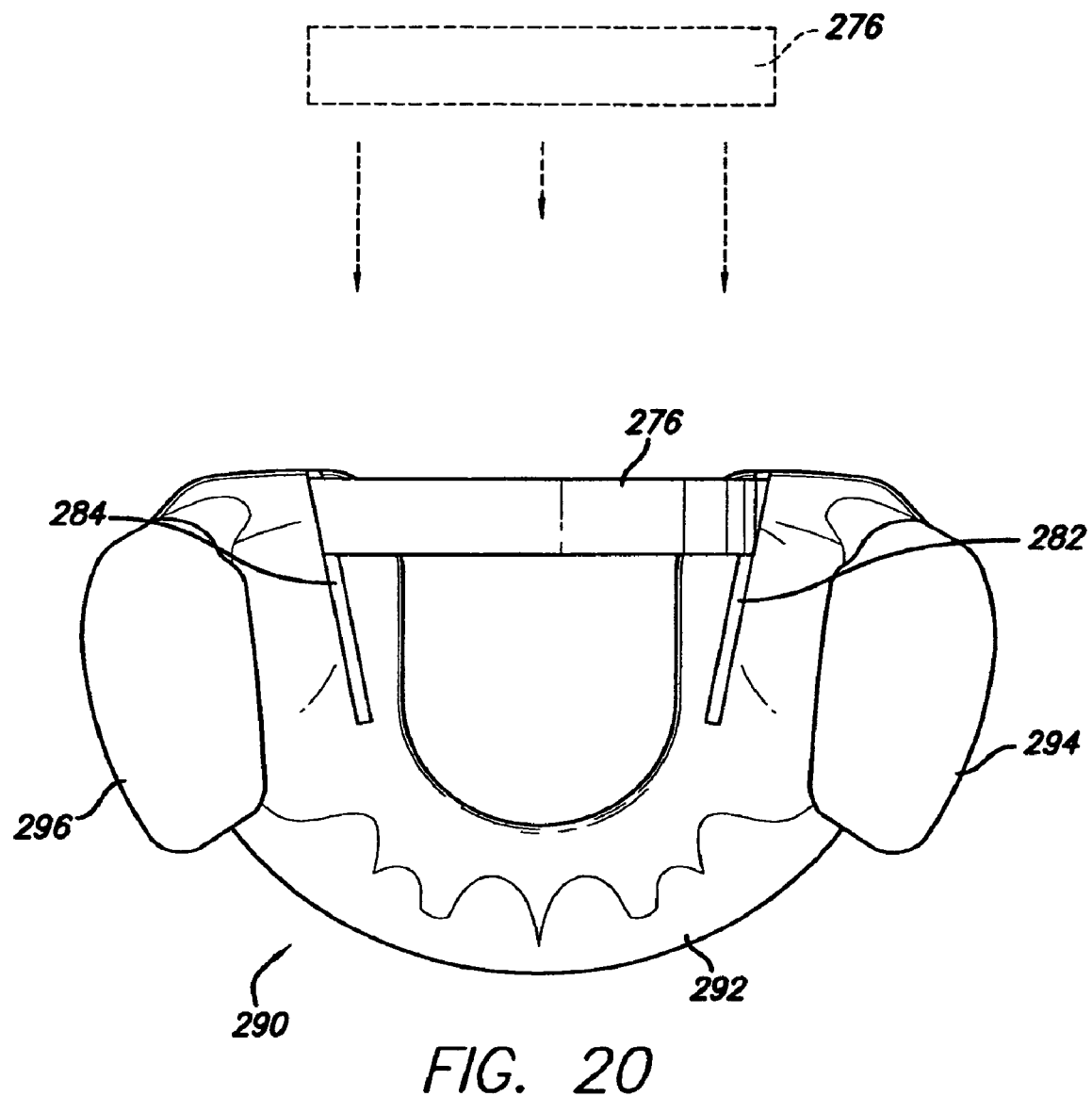

Referring to FIG. 20, there is shown the same device as shown in FIG. 19, except that there is no posterior tongue restrainer.

On any of the above-described embodiments, if it is necessary to advance the mandible to increase the airway even more, acrylic is added to the most lingual portion of the anterior ramp, creating a projection wall that comes off of the anterior ramp at 90 degrees. The lower anterior teeth swing forward and bite forward of this lingual wall. This results in the mandible coming forward to obtain an increased opening.

With a device having posterior ramps, a baseplate, about ½ inch square and about ¼ inch thick, is placed over the right and left posterior ramps, anywhere from the $2^{nd}$ molar to the $1^{st}$ bicuspid.

The curved transpalatal bar, the slidable transpalatal bar and the posterior tongue restrainer, all described herein, may be added to all of the embodiments described in my U.S. Pat. No. 6,766,802, issued on Jul. 27, 2004 and my application Ser. No. 11/165,641, filed Jun. 23, 2005.

All of the devices described herein, which are totally or partially made of plastic, are preferably made of acrylic plastic or talon plastic.

The intra-oral device of this invention may be fitted and sold to any person who suffers from a snoring problem, to effectively reduce or eliminate snoring or sleep apnea.

Having thus described the invention, it is requested that the invention be described by the scope of the following claims.

I claim:

1. A dental oral appliance to open the airway for a sleeping individual who suffers with snoring or obstructive sleep apnea comprising, a body, structure configured to removably affix the appliance to the upper or lower teeth, structure configured to prevent occlusion of the upper and lower teeth, a curved transpalatal member, configured to provide a gap between the transpalatal member and the palate, and a gap between the transpalatal member and the tongue, that extends from the inside of the right molars to the inside of the left molars to inhibit the upward and backward movement of the tongue.

2. The dental oral appliance of claim 1 in which the body has an open palate.

3. The dental oral appliance of claim 1 further comprising a straight or curved posterior tongue restrainer attached to the transpalatal member.

4. The dental oral appliance of claim 1 in which the transpalatal member is curved upward at its center.

5. The dental oral appliance of claim 1 in which the means to removably affix the appliance to the upper or lower teeth comprises an occlusal coverage.

6. The dental oral appliance of claim 1 in which the means to prevent occlusion of the upper and lower teeth comprises a raised incisor ramp that extends from two or more incisors toward the lingual.

7. The dental oral appliance of claim 1 in which the means to prevent occlusion of the upper and lower teeth comprises raised posterior ramps.

8. The dental oral appliance of claim 1 in which the body has a series of recesses to fit against the lingual side of the teeth.

9. The dental oral appliance of claim 1 in which the appliance is made of acrylic plastic.

10. The dental oral appliance of claim 1 further comprising a plurality of raised projections on the bottom of the transpalatal member.

11. The dental oral appliance of claim 1 further comprising structure configured to advance the mandible.

12. The dental oral appliance of claim 11 in which the structure to advance the mandible comprises adding an acrylic wall to the means to prevent occlusion of the upper and lower teeth.

13. A dental oral appliance to open the airway for a sleeping individual who suffers with snoring or obstructive sleep apnea comprising, a body, structure configured to removably affix the appliance to the upper or lower teeth, structure configured to prevent occlusion of the upper and lower teeth, a transpalatal member, configured to provide a gap between the transpalatal member and the palate, that extends from the inside of the right molars to the inside of the left molars to inhibit the upward and backward movement of the tongue in which the transpalatal member is slidably connected to the body.

14. The dental oral appliance of claim 13 in which the transpalatal member has two narrow ribs which slidably fit into two narrow slots in the body.

15. The dental oral appliance of claim 14 further comprising a plurality of raised projections on the bottom of the transpalatal member.

16. The dental oral appliance of claim 13 in which the transpalatal member has edges which slidably fit into narrow slots in the body.

17. A dental oral appliance to open the airway for a sleeping individual who suffers with snoring or obstructive sleep apnea comprising, a body, structure configured to removably affix the appliance to the upper or lower teeth, structure configured to prevent occlusion of the upper and lower teeth, a transpalatal member, configured to provide a gap between the transpalatal member and the palate, and a gap between the transpalatal member and the tongue, that extends from the inside of the right molars to the inside of the left molars to inhibit the upward and backward movement of the tongue further comprising a posterior tongue restrainer attached to the transpalatal member.

18. The dental oral appliance of claim 17 in which the body has an open palate.

19. The dental oral appliance of claim 17 in which the posterior tongue restrainer is attached to the center rear portion of the transpalatal member.

20. The dental oral appliance of claim 17 in which the structure to removably affix the appliance to the upper or lower teeth comprises an occlusal coverage.

21. The dental oral appliance of claim 17 in which the structure to prevent occlusion of the upper and lower teeth comprises a raised incisor ramp that extends from two or more incisors toward the lingual.

22. The dental oral appliance of claim 17 in which the means to prevent occlusion of the upper and lower teeth comprises raised posterior ramps.

23. The dental oral appliance of claim 17 in which the body has a series of recesses, to fit against the lingual side of the teeth.

24. The dental oral appliance of claim 17 in which the appliance is made of acrylic plastic.

25. The dental oral appliance of claim 17 further comprising structure configured to advance the mandible.

26. The dental oral appliance of claim 25 in which the structure to advance the mandible comprises adding an acrylic wall to the structure to prevent occlusion of the upper and lower teeth.

27. A dental oral appliance to open the airway for a sleeping individual who suffers with snoring or obstructive sleep apnea comprising, a body, structure configured to removably affix the appliance to the upper or lower teeth, structure configured to prevent occlusion of the upper and lower teeth, a curved transpalatal member, configured to provide a gap between the transpalatal member and the palate, that extends from the inside of the right molars to the inside of the left molars to inhibit the upward and backward movement of the tongue in which the transpalatal member is slidably connected to the body.

28. The dental oral appliance of claim 27 in which the transpalatal member has two narrow ribs which slidably fit into two narrow slots in the body.

29. The dental oral appliance of claim 27 in which the transpalatal member has edges which slidably fit into narrow slots in the body.

* * * * *